United States Patent [19]
Bryan

[11] Patent Number: 6,103,748
[45] Date of Patent: Aug. 15, 2000

[54] METHOD OF TREATING AN AUTOIMMUNE DISORDER

[76] Inventor: Thomas B. Bryan, 3351 M St., #120, Merced, Calif. 95348

[21] Appl. No.: 09/223,069

[22] Filed: Dec. 29, 1998

Related U.S. Application Data

[60] Provisional application No. 60/090,005, Jun. 19, 1998.
[51] Int. Cl.[7] ........................ A61K 31/415; A61K 31/195
[52] U.S. Cl. ........................ 514/400; 514/561; 514/562; 514/565
[58] Field of Search ........................ 514/400, 561, 514/562, 565

[56] References Cited

U.S. PATENT DOCUMENTS

| 5,112,810 | 5/1992 | Nagai et al. | 514/15 |
| 5,811,446 | 9/1998 | Thomas | 514/399 |
| 5,872,127 | 2/1999 | Cincotta et al. | 514/288 |

*Primary Examiner*—Raymond Henley, Jr.
*Attorney, Agent, or Firm*—Lyon & Lyon LLP

[57] ABSTRACT

A method of administering an amino acid protocol intravenously for the treatment of a patient suffering from an autoimmune disease is provided.

16 Claims, No Drawings

METHOD OF TREATING AN AUTOIMMUNE DISORDER

RELATED APPLICATIONS

This application is related to and claims priority from provisional application Ser. No. 60/090005, filed Jun. 19, 1998.

FIELD OF THE INVENTION

The present invention pertains to the treatment of immunological disorders, including more particularly to the treatment of autoimmune disorders.

BACKGROUND

Autoimmune disease is caused when one's own immune system incorrectly attacks one's own tissue. It is known to treat patients suffering from autoimmune disorders by intravenously introducing immunoglobulin into the patients. A period of remission in the disease can be produced by this treatment. Although the use of immunoglobulin has been relatively effective in the treatment of autoimmune disorders, the mechanism of action is unknown. The intravenous administration of immunoglobulin (IVIG) to any particular patient may cause side effects, such as fever and muscle aches, headaches, nausea and vomiting, dizziness, and tachycardia. There is also the potential of transferring to the patient disease from the person who donated blood used for the manufacture of this immunoglobulin. At a cost of approximately $100/gram, treatment with immunoglobulin is also relatively expensive, amounting to many thousands of dollars for each treatment. There has recently been a shortage in the availability of IVIG.

Standardized parenteral nutritional protocols, which include a combination of amino acids, have been traditionally given to nourish patients who could not be fed orally or gastrically. In one such case, I had used a standardized parenteral nutritional protocol to nourish a patient who had been suffering from an autoimmune disease. The patient, a 70-year old female weighing approximately 40 kg, presented herself to me in 1990 with generalized weakness and ptosis (drooping of the eyelids). The diagnosis of Myasthenia Gravis without Thymoma, an autoimmune disorder, was made following a Tensilon test of the thenar muscle and elevated Acetylcholine receptor antibody titer measured in the blood. The Acetylcholine receptor antibody causes muscle weakness by attacking the muscle endplate, thus interfering with the Acetylcholine synapse between the nerve and the muscle.

The patient regained good strength on a combination of Pyridostigmine and Prednisone, drugs which have been traditionally used to treat the symptoms of Myasthenia Gravis by respectively making more acetylcholine available at the muscle endplate and by reducing the inflammatory response at the muscle end plate plus reducing the amount of antibody formation. The daily administration of Pyridostigmine and Prednisone were continued in order to maintain reasonable control of the symptoms of the disease.

On Nov. 6, 1992, the patient underwent a bowel operation for the correction of an enterorectal fistula. On Nov. 8, 1992, because of her inability to be orally or gastrically fed, the patient was intravenously administered a standardized parenteral nutritional protocol, which was continued for six days until she was discharged from the hospital on Nov. 14, 1992. No change in the patient's Myasthenia Gravis status was noted at this time. As the patient was able to be orally fed, she was not administered the standardized parenteral nutritional protocol after discharge from the hospital. To maintain control of the effects of the Myasthenia Gravis, the patient was continued on Pyridostigmine and Prednisone.

On Nov. 26, 1992, the patient suffered from abdominal discomfort and tenderness and was readmitted to the hospital. Oral feeding ceased, and on Nov. 27, 1992 (Day 1 of the intravenous feeding), I again administered the standardized parenteral nutritional protocol (First Protocol) to the patient at a rate of 100 cc. per hour. The composition of this protocol with the appropriate quantities of each element is set forth in Table 1.

TABLE 1

Individual Elements and the Quantity of each Element in 100 cc of a First Standardized Parenteral Nutritional Protocol

| Elements | Amount |
|---|---|
| Distilled Water | |
| Essential Amino Acids | |
| Isoleucine USP | 0.21 gms |
| Leucine USP | 0.27 gms |
| Lysine as Lysine acetate USP | 0.31 gms |
| Methionine USP | 0.16 gms |
| Phenylalanine USP | 0.17 gms |
| Threonine USP | 0.12 gms |
| Tryptophan USP | 0.046 gms |
| Valine USP | 0.2 gms |
| Non-Essential Amino Acids | |
| Alanine USP | 0.21 gms |
| Arginine USP | 0.29 gms |
| Histidine USP | 0.085 gms |
| Proline USP | 0.34 gms |
| Serine USP | 0.18 gms |
| Glycine USP | 0.42 gms |
| Cystein USP | 0.014 gms |
| Lipids | 10 gms |
| Soybean Oil | * |
| Egg Phosphatides | * |
| Electrolytes | |
| Sodium Chloride | 80 mEq/liter |
| Sodium Phosphate | 25 mEq/liter |
| Potassium Chloride | 30 mEq/liter |
| Calcium Gluconate | 12 mEq/liter |
| Magnesium Sulfate | 8 mEq/liter |
| Zinc Sulfate | 20 mg/liter |
| Trace Elements | |
| Zinc | 5 mg |
| Copper | 2 mg |
| Manganese | 0.5 mg |
| Chromium | 10 mcg |
| Selenium | 60 mcg |
| Daily Vitamins | |
| Ascorbic Acid | 500 mg |
| Vitamin A | 1000 i.u. |
| Vitamin D | 1000 i.u. |
| Thiamine | 50 mg |
| Riboflavin | 10 mg |
| Pyridoxine | 5 mg |
| Niacin | 100 mg |
| Vitamin E | 5 i.u. |
| Dexpanthenol | 25 mg |
| Vitamin K | 10 mg |

On Day 3 of the intravenous feeding, the patient felt much stronger and continued to feel strong for several days thereafter despite having an elevated Acetylcholine receptor antibody titer of 25, with less than 0.5 being normal.

On Day 5 of the intravenous feeding, the patient developed a cholinergic attack secondary to the Pyridostigmine that was continuously administered to her. This resulted in abdominal cramping. The cholinergic attack was relieved by the intravenous administration of Atropine, which countered the effect of Pyridostigmine. The administration of the Pyridostigmine and Prednisone to the patient was discontinued.

On Day 6 of the intravenous feeding, the patient felt strong, despite the discontinuation of the Pyridostigmine and Prednisone.

On Day 7 of the intravenous feeding, the patient continued to get stronger despite the fact that her Acetylcholine receptor antibody titer had risen to 30, a level that typically results in weakness. This indicated to me that the Myasthenia Gravis was not being controlled by the reduction of the Acetylcholine receptor antibody titer, a result typically achieved by the administration of Prednisone, but rather by blocking the effects of the Acetylcholine receptor antibody. Since the administration of the Pyridostigmine had been discontinued, this indicated to me that the effect of the high Acetylcholine receptor antibody titer on the muscle endplates was being countered by the intravenous administration of the First Protocol.

The patient was discharged from the hospital on Dec. 14, 1992, after which she was continued on the First Protocol until Mar. 23, 1993. During this period, the patient's Acetylcholine receptor antibody titer had been measured at 57, 38, and 30 on the respective dates of Jan. 4, 1993, Jan. 25, 1993 and Feb. 18, 1993.

The patient's Myasthenia Gravis continued in remission until Mar. 31, 1993, eight days after the intravenous feeding was discontinued. Two days later, on Apr. 2, 1993, the patient was continued on Pyridostigmine 30 mg twice a day and the patient regained her strength. Although the effects of Myasthenia Gravis typically had to be controlled by a combination of Pyridostigmine and Prednisone, the patient's Myasthenia Gravis continued in partial remission for over 5 months necessitating the use of only Pyridostigmine without the administration of Prednisone. This indicated to me that the intravenous administration of the First Protocol had a prolonged positive effect in treating the Myasthenia Gravis.

On Sep. 13, 1993, the patient had increased weakness and was administered Prednisone 40 mg daily, in addition to the Pyridostigmine. A week later the Prednisone was reduced to 20 mg every other day. The patient was continued on this combination of Pyridostigmine and Prednisone, a treatment that was similar to that given to her prior to the bowel operation. The patient's Acetylcholine receptor antibody titer was measured at 28.7 on Aug. 11, 1993, and at 14 on Oct. 23, 1993, at which time the patient had been continuously administered Prednisone. The patient remained strong until February 1997.

SUMMARY OF THE INVENTION

Through my review of the observations in this case in 1992–1993, I discovered that the administration of the First Protocol to this patient may not only have nourished the patient, but also possibly treated the effects of the Myasthenia Gravis that she had suffered. Although it was standard procedure to administer standardized parenteral nutritional protocols to nourish patients who could not orally or gastrically be fed, it was not known to treat the effects of autoimmune diseases with such protocols when the patient could obtain nourishment orally or gastrically.

To determine to what extent the effects of autoimmune diseases could be treated through the administration of standardized parenteral nutritional protocols, with subjects who can orally or gastrically be fed, I performed case studies to obtain more information on my discovery. Those test cases are described herein and indicate that my discovery is useful in treating autoimmune diseases with an amino acid protocol in patients who can obtain nutrition orally or gastrically.

My present invention thus comprises a novel method of treating a patient suffering from an autoimmune disorder by intravenously administering an amino acid protocol to the patient when the patient obtains nourishment orally or gastrically. The amino acid protocol includes at least one amino acid and may also include other nutrients and vitamins to further facilitate the restoration of the patient's immune system.

DESCRIPTION

I have discovered through tests conducted on two patients who had respectively suffered from Myasthenia Gravis and Guillain-Barré like syndrome, both of which are autoimmune diseases, that patients suffering from autoimmune disorders can be effectively treated through the intravenous administration of amino acids, such as, e.g., the amino acid compositions found in standardized parenteral nutritional protocols.

First Case Study

The first test involved as its subject, the patient for which I had treated the effects of Myasthenia Gravis during the 1990–1993 time period. This patient had presented herself to me in February of 1997 after suffering from a bout of weakness caused by the Myasthenia Gravis. Because of the marked worsening of her myasthenia, and based on my previous observations of the patient during her treatment with the First Protocol in 1992–1993, I decided to perform a case study on the patient, with the patient's consent, to determine if the effects of the Myasthenia Gravis could, in fact, be treated with another standardized parenteral nutritional protocol (Second Protocol).

To determine if different standardized parenteral nutritional protocols could treat the effects of autoimmune diseases, I decided to vary the composition of the Second Protocol from the First Protocol. The composition of the Second Protocol with the appropriate quantities of each element is set forth in Table 2.

TABLE 2

| Individual Elements and the Quantity of each Element in 100 cc of a Second Standardized Parenteral Nutritional Protocol ||
|---|---|
| Elements | Amount |
| Distilled Water ||
| Essential Amino Acids ||
| Isoleucine USP | 0.59 gms |
| Leucine USP | 0.77 gms |
| Lysine as Lysine acetate USP | 0.87 gms |
| Methionine USP | 0.45 gms |
| Phenylalanine USP | 0.48 gms |
| Threonine USP | 0.34 gms |
| Tryptophan USP | 0.13 gms |
| Valine USP | 0.56 gms |
| Non-Essential Amino Acids ||
| Alanine USP | 0.60 gms |
| Arginine USP | 0.81 gms |

TABLE 2-continued

Individual Elements and the Quantity of each Element in 100 cc of a Second Standardized Parenteral Nutritional Protocol

| Elements | Amount |
| --- | --- |
| Histidine USP | 0.24 gms |
| Proline USP | 0.95 gms |
| Serine USP | 0.56 gms |
| Glycine USP | 0.19 gms |
| Cystein USP | 0.014 gms |
| Glycerin as Glycerol | 3 gms |
| Electrolytes | |
| Calcium Glucanate | 9.2 mEq/liter |
| Sodium Chloride | 45.0 mEq/liter |
| Potassium Acetate | 30.0 mEq/liter |
| Magnesium Sulfate | 8.1 mEq/liter |
| Potassium Phosphate | 10.0 mmoles/liter |
| Sodium | 10.0 mEq/liter |
| Phosphate | 20.0 mmoles/liter |
| Acetate | 72.0 mEq/liter |
| Chloride | 3.0 mEq/liter |
| Multi-Vitamins (Daily Amounts) | |
| Ascorbic Acid | 100 mg |
| Vitamin A | 1 mg |
| Vitamin D | 5 mcg |
| Thiamine | 3 mg |
| Riboflavin | 38 mg |
| Pyridoxine | 4 mg |
| Niacin | 40 mg |
| Vitamin E | 10 mg |
| Dexpanthenol | 15 mg |
| Biotin | 60 mcg |
| Folic Acid | 400 mcg |
| Cyanocobalamin | 5 mcg |

The patient was administered the Second Protocol set forth in Table 2 for a period of 17 hours, notwithstanding the fact that the patient could obtain nutrition orally. After such treatment, the patient felt strong and was discharged from the hospital. She was continued on Pyridostigmine 30 mg. twice daily and Prednisone 20 mg every other day.

On Apr. 13, 1997, the patient suffered from anemia and abdominal pain and was readmitted to the hospital. Oral feeding and the administration of the Pyridostigmine and Prednisone were discontinued. Two days later, on Apr. 15, 1997, the patient was again administered the Second Protocol at a rate of 84 cc. per hour. Intravenous feeding was discontinued on Apr. 18, 1997, at which time the patient felt much stronger. The patient was discharged from the hospital on the same day, and the administration of the Pyridostigmine and Prednisone were not renewed. During this time period the patient had been administered 4,260 cc. of the Second Protocol. As of the filing of this application, the patient's Myasthenia Gravis has been in remission.

This case study, in conjunction with the second case study discussed further below, indicates to me that the effects of an autoimmune disease suffered by a patient can successfully be treated through the administration of an amino acid protocol.

Second Case Study

In the second test, a 77-year old female weighing approximately 58 kgs. presented herself to me in August of 1997. She had previously developed a case of giardiasis and became weak afterwards. The weakness was progressive, however, and on the day of admission, the patient fell to the ground due to the weakness in her legs, and was unable to arise. Her examination revealed marked weakness of the pelvic girdle musculature. The patient was unable to raise either leg off the bed. There was also moderate weakness of the shoulder girdle muscles. Strength was better distally in the extremities. Deep tendon reflexes (DTR's) were absent except for mild reflexes at the knees. There was a mild stocking type of pinprick loss distally in her legs.

A spinal tap was done and her CSF protein was reported as normal. She did, however, have significantly prolonged H-reflexes suggesting disease of the proximal nerves or nerve roots. She also was found to have the syndrome of secretion of inappropriate amounts of ADH (SIADH). This syndrome can occur due to Guillain-Barré like syndrome.

As a treatment, the patient was intravenously administered 100 mg of SoluMedrol daily. The patient, however, continued to have weakness. As she showed no significant improvement, on the 12th day of hospitalization, I decided to perform a second case study, with the patient's consent, to determine if the favorable treatment of the effects of another type of autoimmune disease could be repeated through the administration of a standardized parenteral nutritional protocol. The patient was administered the Second Protocol at a rate of 100 cc. per hour, notwithstanding the fact that the patient could be fed orally.

Though the patient had reported that she had gained a little strength during the previous twelve days prior to the intravenous administration of the Second Protocol, she was still unable to raise either leg off the bed. Approximately 6 hours after the initial intravenous administration of the Second Protocol, however, the patient was able to raise her right leg off the bed.

After 36 hours of the initial intravenous administration of the Second Protocol, the patient felt strong and was readily able to raise both her legs off the bed. After 5 days of the initial intravenous administration of the Second Protocol, the patient was able to walk unassisted and was discharged from the hospital. The patient was evaluated 2 days later and continued to be strong. As of the filing of this application, the patient still had not suffered a relapse of the weakness.

Thus, two case studies have been presented in which the effects of Myasthenia Gravis and Guillain-Barré, both autoimmune diseases, were treated with standardized parenteral nutritional protocols. This indicates that my discovery that an amino acid protocol can be intravenously administered to a patient to treat the effects of autoimmune diseases, such as, e.g., Myasthenia Gravis and Guillain-Barré like syndrome, is useful.

Thus, an improved method for administering an amino acid protocol for a patient suffering from an autoimmune disorder is disclosed. While methods of this invention have been shown and described, it would be apparent to those skilled in the art that many more modifications are possible without departing from the inventive concepts herein.

The invention, therefore is not to be restricted except in the spirit of the appended claims.

What is claimed:

1. A method of treating an autoimmune disease in a patient suffering therefrom, the method comprising:
   intravenously administering an amino acid protocol to said patent, said patient capable of being orally or gastrically nourished.

2. A method of treating Myasthenia Gravis in a patient suffering therefrom, the method comprising:
   intravenously administering an amino acid protocol to said patient, said patient capable of being orally or gastrically nourished.

3. A method of treating Guillain Barré like syndrome in a patient suffering therefrom, the method comprising:

intravenously administering an amino acid protocol to said patient, said patient capable of being orally or gastrically nourished.

4. A method of treating an autoimmune disease in a patient suffering therefrom, the method comprising:

intravenously administering an amino acid protocol to said patient, said patient capable of being orally or gastrically nourished, wherein said amino acid protocol comprises at least one essential amino acid.

5. The method of claim 4, wherein said amino acid protocol comprises at least one of Isoleucine, Leucine, Lysine, Methionine, Phenylalanine, Threonine, Tryptophan and Valine.

6. The method of claim 1, wherein said amino acid protocol comprises at least one non-essential amino acid.

7. The method of claim 1, wherein said amino acid protocol comprises at least one of Alanine, Arginine, Histidine, Proline, Serine, Glycine and Cystein.

8. The method of claim 1, wherein said amino acid protocol comprises at least one of Isoleucine, Leucine, Lysine, Methionine, Phenylalanine, Threonine, Tryptophan, Valine, Alanine, Arginine, Histidine, Proline, Serine, Glycine and Cystein.

9. A method of treating an autoimmune disease in a patient suffering therefrom, the method comprising:

intravenously administering an amino acid protocol to said patient, said patient capable of being orally or gastrically nourished, wherein said amino acid protocol comprises an essential amino acid, a non-essential amino acid, a lipid, an electrolyte and a vitamin.

10. A method of treating an autoimmune disease in a patient suffering therefrom, the method comprising:

intravenously administering an amino acid protocol to said patient, said patient capable of being orally or gastrically nourished, wherein said amino acid protocol comprises an essential amino acid, a non-essential amino acid, a glycerin, an electrolyte and a vitamin.

11. The method of claim 1, wherein the patient is administered the amino acid protocol until the autoimmune disease abated.

12. The method of claim 2, wherein the patient is administered the amino acid protocol until the Myasthenia Gravis abates.

13. The method of claim 3, wherein the patient is administered the amino acid protocol until the Guillain Barré like syndrome abates.

14. The method of claim 4, wherein the patient is administered the amino acid protocol until the autoimmune disease abates.

15. The method of claim 9, wherein the patient is administered the amino acid protocol until the autoimmune disease abates.

16. The method of claim 10, wherein the patient is administered the amino acid protocol until the autoimmune disease abates.

* * * * *